(12) United States Patent
Divoky et al.

(10) Patent No.: US 11,523,781 B2
(45) Date of Patent: Dec. 13, 2022

(54) METHOD FOR RUNNING A COLLISION PROTECTION SYSTEM FOR A MEDICAL OPERATING DEVICE, MEDICAL OPERATING DEVICE, COMPUTER PROGRAM, AND DATA STORAGE MEDIUM

(71) Applicant: Siemens Healthcare GmbH, Erlangen (DE)

(72) Inventors: Robert Divoky, Forchheim (DE); Thomas Fuchs, Buckenhof (DE); Patrick Kugler, Erlangen (DE); Philip Mewes, Nuremberg (DE); Karl-Ernst Strauss, Dormitz (DE); Tamäs Ujvári, Forchheim (DE); Angelika Zinecker, Cadolzburg (DE)

(73) Assignee: Siemens Healthcare GmbH, Erlangen (DE)

( * ) Notice: Subject to any disclaimer, the term of this patent is extended or adjusted under 35 U.S.C. 154(b) by 844 days.

(21) Appl. No.: 16/343,524

(22) PCT Filed: Oct. 9, 2017

(86) PCT No.: PCT/EP2017/075653
§ 371 (c)(1),
(2) Date: Apr. 19, 2019

(87) PCT Pub. No.: WO2018/077604
PCT Pub. Date: May 3, 2018

(65) Prior Publication Data
US 2019/0261932 A1    Aug. 29, 2019

(30) Foreign Application Priority Data
Oct. 27, 2016  (DE) ..................... 10 2016 221 222.2

(51) Int. Cl.
*A61B 6/10* (2006.01)
*A61B 34/30* (2016.01)
(Continued)

(52) U.S. Cl.
CPC .............. *A61B 6/102* (2013.01); *A61B 34/30* (2016.02); *B25J 9/1674* (2013.01); *B25J 9/1676* (2013.01);
(Continued)

(58) Field of Classification Search
CPC ....... A61B 6/102; A61B 34/30; A61B 6/4441; A61B 2090/376; B25J 9/1674; B25J 9/1676
See application file for complete search history.

(56) References Cited

U.S. PATENT DOCUMENTS 10,646,296 B2 *  5/2020  Hasegawa .............. A61B 34/74
2007/0120512 A1    5/2007  Albu-schaffer
(Continued)

FOREIGN PATENT DOCUMENTS

DE   102005054575 B3   4/2007
DE   102013110905 A1   4/2015
(Continued)

OTHER PUBLICATIONS

German Office Action for German Application No. 10 2016 221 222.2 dated Aug. 17, 2017.
(Continued)

*Primary Examiner* — Basil T. Jos
(74) *Attorney, Agent, or Firm* — Lempia Summerfield Katz LLC

(57) ABSTRACT

A method is provided for running a collision protection system for a medical operating device, which has a patient bed for a patient to be operated on, an image recording device having at least one movable image recording component for recording image data of the patient during the operation, and an assistance robot having a movable assistance component which during the operation is situated at least temporarily inside the patient and/or is coupled in (Continued)

terms of movement to an instrument situated inside the patient. In the method, an item of criticality information is determined which describes the criticality of possible collisions of components of the operating device and/or movements of the patient with regard to the interaction of the assistance robot with the patient. Depending upon the criticality information, when a criticality criterion indicating a raised criticality, (e.g., a criticality exceeding a threshold value), is met, a safe mode of operation of the collision protection system is activated, which meets higher safety requirements than a normal mode of operation.

18 Claims, 2 Drawing Sheets

(51) Int. Cl.
  *B25J 9/16* (2006.01)
  *A61B 6/00* (2006.01)
  *A61B 90/00* (2016.01)
(52) U.S. Cl.
  CPC ....... *A61B 6/4441* (2013.01); *A61B 2090/376* (2016.02)

(56) References Cited

U.S. PATENT DOCUMENTS

| | | | |
|---|---|---|---|
| 2010/0204713 A1* | 8/2010 | Ruiz Morales | B25J 9/041 606/130 |
| 2014/0163736 A1 | 6/2014 | Azizian | |
| 2015/0239124 A1 | 8/2015 | Haddadin | |
| 2015/0366546 A1* | 12/2015 | Kamen | A61B 5/055 600/461 |
| 2016/0144509 A1 | 5/2016 | Gulhar | |
| 2016/0242849 A9 | 8/2016 | Crawford | |
| 2016/0297074 A1 | 10/2016 | Divoky | |

FOREIGN PATENT DOCUMENTS

| | | |
|---|---|---|
| DE | 102014223771 A1 | 5/2016 |
| DE | 102015206511 A1 | 10/2016 |

OTHER PUBLICATIONS

PCT International Search Report and Written Opinion of International Searching Authority dated Feb. 9, 2018, corresponding to PCT International Application No. PCT/EP2017/075653.

* cited by examiner

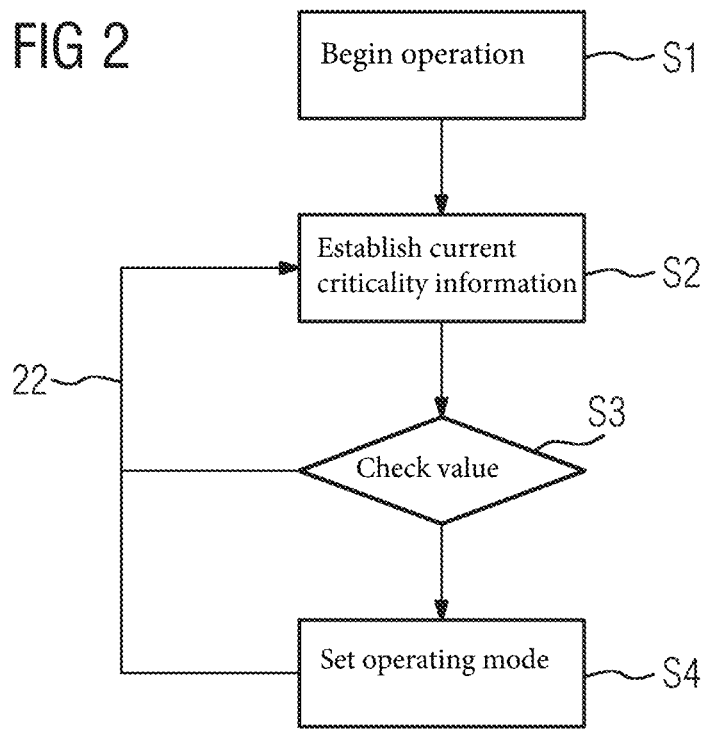

METHOD FOR RUNNING A COLLISION PROTECTION SYSTEM FOR A MEDICAL OPERATING DEVICE, MEDICAL OPERATING DEVICE, COMPUTER PROGRAM, AND DATA STORAGE MEDIUM

The present patent document is a § 371 nationalization of PCT Application Serial No. PCT/EP2017/075653, filed Oct. 9, 2017, designating the United States, which is hereby incorporated by reference, and this patent document also claims the benefit of German Patent Application No. DE 10 2016 221 222.2, filed Oct. 27, 2016, which is also hereby incorporated by reference.

TECHNICAL FIELD

The disclosure relates to a method for operating a collision protection system for a medical operating device, which has a patient couch for a patient to be operated on, and an assistance robot, having a movable assistance component which during the operation is situated at least temporarily inside the patient and/or is coupled in terms of movement to an instrument situated inside the patient. In addition, the disclosure relates to a medical operating device, to a computer program, and to an electronically readable data storage medium.

BACKGROUND

Nowadays a plurality of medical interventions, (e.g., operations), also take place with imaging supervision. Image recording devices may be used for this purpose, which restrict the space needed for the operation as little as possible or only restrict it at times. X-ray devices with a C-arm, on which an x-ray emitter and an x-ray detector are arranged opposite one another, are an example of this. The C-arm may be moved into a position in which it impedes the person carrying out the operation as little as possible, or may even be removed entirely from the operation area, by the patient being supported on a patient couch. It has been proposed for this purpose, for example, that the C-arm be arranged on a robot arm, in order to be able to provide a greatest possible number of degrees of freedom of movement.

What is more, it has already been proposed in the prior art that further assistance be provided during operations by assistance robots. These types of assistance robot may be embodied as lightweight robots (LWR), for example, and serve various purposes. Known assistance robots provide guidance aids for medical instruments, for example, in the form of sleeves or hoses, which serve to guide the medical instrument. For example, a needle or a drill may be explicitly guided into the patient to be operated on as a medical instrument via an assistance component of an assistance robot serving as a guidance aid. Assistance robots are also conceivable in which an assistance component itself is introduced into the patient.

In such medical operating devices, (which may include the patient couch, the assistance robot, and the image recording device), collision protection, in particular in respect of the patient, is an important topic, because a plurality of components exist that may also be moved independently, (e.g., image recording components such as the C-arm and/or assistance components of the assistance robot and/or the patient couch). Thus, collision protection systems have already been proposed for such medical operating devices, which may use sensor systems, such as proximity switches, movement data of various drives, mathematical models for simulation, and the like. For a large part of the time during which such systems are in use during operations, simple mechanisms, (e.g., an evaluation of data from proximity sensors), are entirely adequate. When an assistance robot is used, it may occur however that the assistance components of the assistance robot are coupled in terms of movement to the patient, in particular, if these are situated at least temporarily inside the patient or in their turn are coupled in terms of their movement to a medical instrument, which is situated at least temporarily in the patient. In such cases, problems may result, even with more minor collisions, if a sensitive region of the patient is being treated or examined during the operation. In this regard, it has already been proposed, for taking further safety measures in such medical operating devices, to greatly reduce the speed of movement of all movable components, for example. This leads to difficulties in the working sequence, because the duration of the operation may be greatly lengthened or a much greater effort also arises on the part of the people carrying out the intervention.

SUMMARY AND DESCRIPTION

The scope of the present disclosure is defined solely by the appended claims and is not affected to any degree by the statements within this summary. The present embodiments may obviate one or more of the drawbacks or limitations in the related art.

The underlying object of the disclosure is to specify a possibility for realizing a collision protection system, in which an outstanding safety for the patient without too great a restriction of the usability of the operating device is realized.

To achieve this object, in a method of the type stated at the outset, that, taking into account the workflow data describing the current operation phase in an operation workflow, an item of criticality information, which describes the criticality of possible collisions between components of the operating device and/or movements of the patient with regard to the interaction of the assistance robot with the patient, is established, wherein depending on the criticality information, on fulfillment of an increased criticality criterion, in particular indicating a criticality exceeding a threshold value, a safe operating mode of the collision protection system satisfying a higher safety requirement than the normal operating mode is activated.

The operating device may also have an image-recording device with at least one movable image-recording component for recording image data of the patient during the operation. The disclosure may also be applied to further subsystems of the operating device, (e.g., a further, second assistance robot and its assistance components).

Thus, a collision protection system is initially realized that may be operated in any event in a number of different operating modes, so that an adaptive tailoring to the current risk existing for the patient is provided. Within each operating mode calculation processes may be carried out in order to calculate collision values, including a collision probability, for example. The collision values may be evaluated by at least one measure criterion, for which, if fulfilled, measures are carried out, (for example, a warning and/or an alarm is output), existing movements carried out automatically and/or manually are stopped, and the like. In a normal operating mode, the system operates with a slightly lower safety requirement because minor collisions of components of the operating device with one another and/or with people are less critical. If an increased risk exists for the patient, (e.g., because of a coupling in terms of movement between the assistance robot and the patient), a safe operating mode is activated, in which higher safety requirements are imposed, (e.g., collisions may be avoided completely with a high degree of safety). In this way, the transmission of shocks/collisions to an instrument situated inside the patient may be prevented. Higher safety requirements in the at least one safe operating mode may be fulfilled in such cases in a variety of ways, as will be explained in more detail below with reference to concrete examples. The accuracy of calculation, the reliability of calculation, the intervention threshold, the quality of underlying sensor data, and/or other aspects may be improved.

In order to select a current operating mode of the collision protection system to be used, criticality information is established, which describes the criticality of possible collisions of components of the operating device and/or movements of the patient in relation to the interaction of the assistance robot with the patient, in particular, within a control device realizing the collision protection itself. The criticality information in this case may be determined in the form of at least one criticality value. To establish the criticality information, the current operation workflow is taken into account, wherein workflow data describing the workflow is included in the determination. The beginning and the end of critical states for the patient may be derived from the operation workflow (e.g., monitored or supported centrally by a control device), because it may be deduced from the current operation phase whether, for example, a movement coupling between the patient and the assistance robot exists or will exist at least for some of the time during this operation phase.

Because it is thus largely sufficient to use the normal operating mode of the collision protection system, (e.g., in the positioning of the patient in the operating theatre (OP) and when undertaking a registration between the assistance robot and the image recording device), the people carrying out the operation are not restricted in their workflow by excessive safety measures. Improved safety mechanisms are only employed by activating the safe operating mode when these are really needed, for which the current operation phase in the workflow is analyzed. Thus computing-intensive, workflow-impeding, and/or slow safety mechanisms only come into force when a greater risk would actually arise for the patient during the use of the normal operating mode.

In this case, there may be provision that, when a switching back criterion is fulfilled, (e.g., when the threshold is not met), the system switches back into the previous operating mode. The safe operating mode is then only active for as long as the critical situation obtains for the patient. The switching back criterion may be the fact that the fulfillment of the criticality criterion no longer applies.

In this case, it may also be expedient to realize a graduated safety concept, in that a number of criticality criteria are used, wherein if a criticality criterion is fulfilled, a safe operating mode assigned to the criterion is activated. In particular, criticality intervals beginning from the assigned threshold value in each case may be used for a number of safe operating modes, wherein for criticality information describing a criticality lying within this criticality interval, the safe operating mode assigned to this is activated. In this way, ultimately a type of fine graduation to the criticality, as is produced in particular from the workflow data, is realized, so that in particular the use of measures that impede the workflow and/or slow down the progress of the operation may be graded act-by-act according to their necessity.

In a first advantageous, concrete embodiment, there may be provision that, in at least one of the at least one safe operating modes, at least one calculation process carried out within the framework of the collision protection, (e.g., to establish a collision probability), is carried out redundantly as regards the hardware and/or the software, wherein all results obtained during the redundant calculation are taken into account for the collision protection, and/or are carried out with an increased calculation accuracy. For example, there may be provision for a second collision calculation device to be realized, (e.g., for at least one further processor and/or core to be used), in order to realize hardware redundancy. Different software may also be used, wherein the redundant calculation may be carried out at least partly in a diversified way, in particular, in respect of algorithms used for the calculation process. Diversified denotes that the hardware used and/or the software used also differs for the redundant calculation ways, thus in particular different algorithms are employed, in order to establish in this way whether the same result is then obtained with the two ways of calculating it, thus to make a plausibility check possible. The use of redundant ways of calculation also has the advantage that, if one of the ways of calculation fails, the other ways of calculation may be used to provide a failsafe mechanism.

As a second concrete embodiment which may be used in addition or as an alternative to the first concrete embodiment, there may be provision, in at least one of the at least one safe operating modes, for a movement of at least one of the components of the medical operating device only to be carried out after detection of a confirmation action of an operator. Thus, if there is a critical state, (e.g., a coupling of the movement of the assistance robot with the patient), a confirmation action is required at least for movement of relevant components, regardless of whether this occurs manually and/or automatically. In such cases, the components needing a confirmation action to be moved may expediently be grouped into a safety group of components. A safety group of components of this type may include the image recording components, the patient couch, and the assistance components. This is based on the knowledge that not all components of the medical operating device necessarily deliver relevant collisions, so that there may be a restriction to the components for which the increased risk of collisions actually exists, thus, in particular, also the patient couch, the imaging components (e.g., a C-arm), and the assistance robot or the assistance robot components themselves. Such a safety group of components may also be used expediently in other embodiments, as will be explained in greater detail below.

For a manual ability to move the corresponding components, (for example, a movement of the patient couch by a joystick or another operating lever), there may thus be provision that in the safe operating mode a confirmation action is required in addition, (for example, the actuation of a confirmation button), in order to actually also be able to make the movement by the operating element assigned to the movement. Such operating elements, which refers to both an operating element for the confirmation action and also an operating element for the movement of components of the medical operating device, may be provided on an operating console of the medical operating device.

As far as provision for movements of relevant components of the medical operating device carried out automatically is concerned, an expedient development may make provision for a visualized representation of the planned movement to be displayed on a display device with the request for a confirmation action. The operator may evaluate the movement to be undertaken and assess whether it may represent a danger for the patient.

A confirmation operating element may be used for accepting the confirmation operating action, wherein the confirmation operating element may be kept actuated during the entire movement of the component. In this way, it may be insured that a person carrying out the operation monitors the movement process with particular care and that they are made aware of the criticality of the operation phase.

A third concrete embodiment of the safe operating mode, which is naturally also able to be combined with the other embodiments, makes provision for, in at least one of the at least one safe operating mode, a movement speed of at least one component, (in particular of all components), to be limited by a upper safety limit value that is lower than a normal limit value used outside the safe operating mode. For example, there may be provision for the safety limit value to amount to just 10% or less of the normal limit value, (for example, 1 mm/s or less). This indicates that, within the safe operating mode, at least components of the safety group, (if necessary all components too), will be moved far more slowly than in the normal operating mode, so that collisions may be detected far earlier both by users and also by the collision protection system and there are no risks that stopping a component would take too long, so that a collision may still arise despite the system. What is more, possible collisions, if they still occur, are greatly ameliorated.

In a further concrete embodiment of the safe operating mode able to be combined with other embodiments, there may be provision, in at least one of the at least one safe operating modes, for at least one measure parameter, describing the initiation of measures, of a measure criterion used in the collision protection system to be configured for earlier initiation compared with the normal operating mode and/or for additional measures and/or measure criteria to be used. Thus, in this example, to increase the safety in safe operating mode, there may be provision for increasing safety margins, (e.g., distances to be maintained between the components and/or people), which may lead to an earlier response of the collision protection system and thus to an improved avoidance of collisions. There may also be provision for using further measure criteria and/or further measures and/or for adapting measure parameters for carrying out the measures, for example, connecting-in new warning tones, braking more quickly, and the like.

In an additional embodiment, which may be combined with other concrete embodiments, for realizing the safe operating mode, there may be provision that, in at least one of the at least one safe operating modes, at least one collision sensor deactivated in normal operating mode is activated and its sensor data is taken in to account in calculation processes for collision protection. This type of collision protection sensor may involve an ultrasound distance measurement sensor and/or a sensor arranged on the image recording component. In the overall system, (e.g., the medical operating device), collision protection sensors may thus be provided, which are only actively switched in the safe operating mode, for example, because they would deliver too many false triggers outside the safe operating mode. An example for such sensors is ultrasound distance measurement sensors, which are arranged on the imaging component, (for example, a C-arm, x-ray detector, and/or x-ray emitter arranged thereon). Such ultrasound distance measurement sensors would frequently also detect hand movements in the operating area and the like, which may lead to false triggerings. If there is a higher criticality, this risk may be taken into account instead, in order to increase the safety overall by a larger database.

In certain examples, a central control device of the medical operating device monitoring the progress of the operation may be used, wherein the medical operating device establishes the workflow data. Control devices embodied in this way, which guide a person carrying out the operation through the workflow of the operation and/or support them in such cases, have already basically been proposed in the prior art, so that an operating device with such a control device already knows useful workflow data, from which the criticality of the current operation phase may be derived.

Expediently, the workflow data may be established at least in part from sensor data of monitoring sensor monitoring the operation area and/or from image data of the image recording device registered with the assistance robot. It is thus conceivable that image data of the image recording device may also be evaluated, in order to determine, for example, whether or not the assistance component and/or a medical instrument coupled to the assistance component is already interacting with the patient. Medical instruments may be detected in the image data of the image recording device, for instance, an x-ray device with a C-arm, so that, even in a simple evaluation, correspondingly useful workflow data may be established and criticality information may be derived therefrom. In certain examples, dedicated monitoring sensors may be used, which may also be used within the framework of the actual collision protection system, e.g., in normal operating mode and/or in safe operating mode. A concrete realization of such a monitoring sensor may make provision, for example, for the assistance component recording an instrument as a monitoring sensor to have a closed contact switch from an instrument coupled in terms of movement. Thus, as soon as the medical instrument is used in the assistance component, which may serve as a guide for the instrument, for example, the contact switch is actuated automatically and the information about the beginning of a critical operation phase is available. A plurality of other concrete embodiments of such monitoring sensors is also possible and conceivable.

In one concrete embodiment, there may be provision for the criticality information to establish an increased criticality for workflow data describing a completed registration between the image recording device and the assistance robot and/or a conclusion of a trajectory moving towards the patient of the assistance component and/or a movement coupling of an instrument with the assistance component. A critical state is thus described, for example, with respect to the starting time, by a concluded registration of the image recording device and the assistance robot or the concluded movement of a trajectory of the assistance component, which in a further act would make it possible to introduce a medical instrument into the patient. It is precisely with a graduated process that it may prove expedient to include these types of operation phase in the operation workflow, for example, by a first increase in safety being undertaken by a first safe operating mode after conclusion of the registration, but the safety being greatly increased again however as soon as a movement coupling between the assistance robot and the patient may occur or occurs (second safe operating mode). Accordingly, there may be a switch back again when the movement coupling is no longer in place and thus the criticality is lowered.

As a possibility for realizing a safe operating mode making available enhanced safety, it is also conceivable to increase the accuracy of the calculation processes. There may be provision here, for example, instead of a calculation with spherical objects, which are checked as to whether they overlap, for the system to work in safe operating mode with surface meshes as surface descriptions. Other variants to increase the accuracy of the calculation are also conceivable.

An expedient development advantageously makes provision that, for reducing the calculation effort, the components of the medical operating device considered within the framework of calculation processes of the collision protection are restricted, in particular, to the safety group. At least in respect of collisions that affect the patient, the collision calculation may thus be restricted to the components that are relevant in relation to the critical state, thus the components of the safety group, (e.g., the patient couch, the image recording component, and the assistance component). If this is combined, for example, with a redundant calculation in the safe operating mode, the additional calculation path may be restricted to the components of the safety group, for example. In this way, savings are made in calculation effort.

As well as the method, the disclosure also relates to a medical operating device, which has a patient couch for a patient to be operated on, an image recording device with at least one movable image recording component for recording image data of the patient during the operation, and an assistance robot, having a movable assistance component, which during the operation is situated at least temporarily inside the patient and/or is coupled in terms of movement to an instrument situated inside the patient, which is characterized by a control device embodied for carrying out the method, realizing a collision protection system. All statements made in relation to the method may be transferred analogously to the medical operating device, with which the advantages already stated may likewise be obtained.

A computer program may be able to be loaded directly into a memory of a control device of a medical operating device and may have program code for carrying out the acts of a method described herein, when the computer program is executed in the control device. The computer program may be stored on an electronically-readable data storage medium, which includes electronically-readable control information stored thereon, which includes a computer program which is embodied such that, when the data storage medium is used in a control device of the medical operating device, it carries out a method described herein. The data storage medium may involve a non-transient data storage medium, (e.g., a CD-ROM).

BRIEF DESCRIPTION OF THE CLAIMS

Further advantages and details of the present disclosure emerge from the exemplary embodiments described below and also with reference to the drawings.

FIG. 2 depicts a flow diagram of an exemplary embodiment.

DETAILED DESCRIPTION

Figure 1:
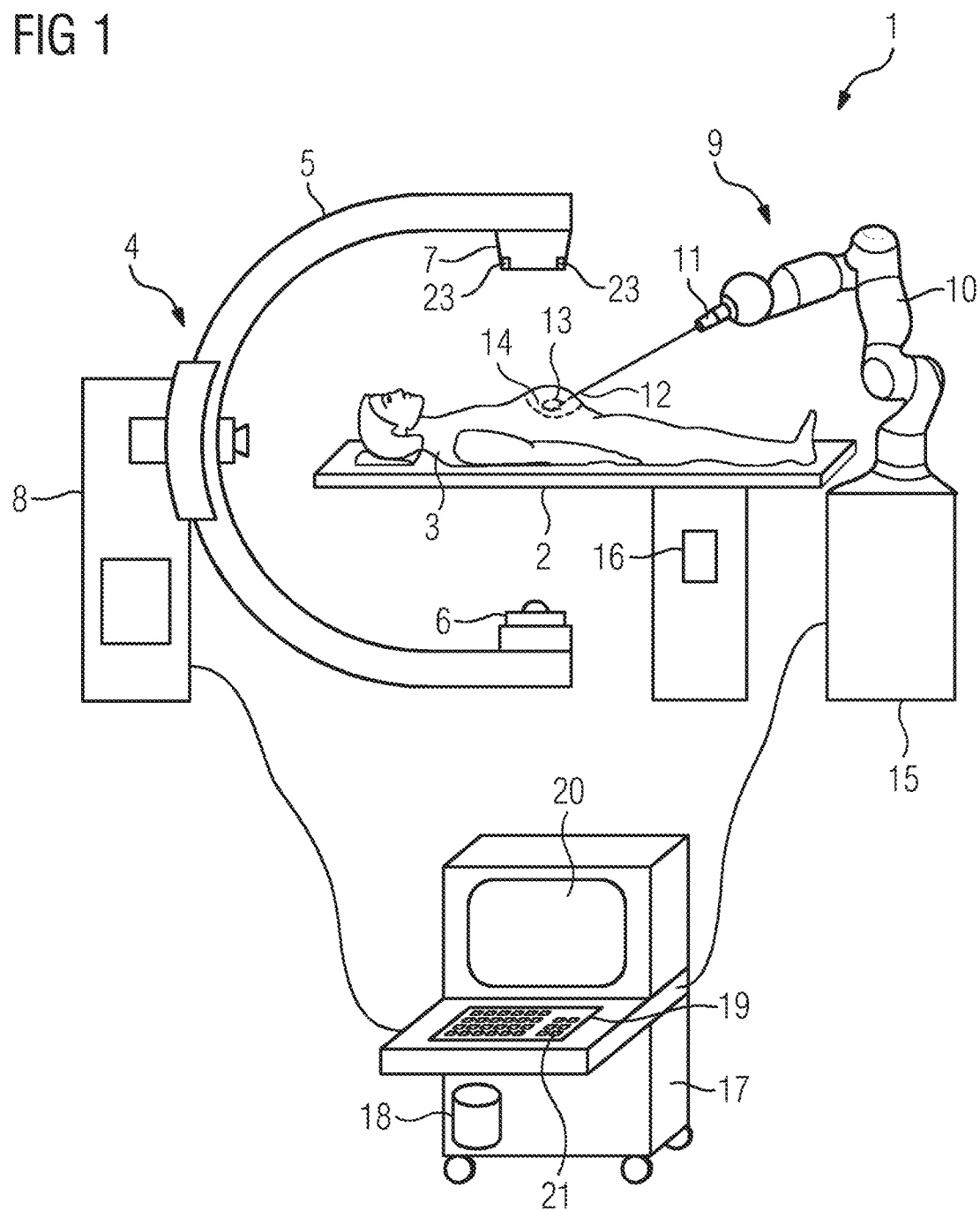
FIG. 1 depicts an example of a medical operating device.

FIG. 1 depicts a basic diagram of a medical operating device 1. A patient 3 to be operated on, also indicated here, may be supported on a patient couch 2, which may also be referred to as a patient table. The operating device 1 also includes an image recording device 4, here an x-ray device with a C-arm 5, on which an x-ray emitter 6 and an x-ray detector 7 are arranged opposite one another. The C-arm 5 is attached, so that it is able to be moved in at least one degree of freedom, on a stand 8 or on a robot arm not shown here.

The operating device 1 further includes an assistance robot 9, which has an assistance component 11 able to be adjusted via a robot arm 10 in a number of degrees of freedom, which in this figure serves as a guide for a medical instrument 12 likewise shown here for the sake of clarity. If the medical instrument 12 is guided inside the assistance component 11, it may be inserted precisely targeted into a target area 13 in the patient 3, for example, a tumor to be treated and/or anatomical components of the spinal column. The treatment region 14 shown here is thus only to be understood as an example.

The robot arm 10 is supported here by an if necessary mobile stand 15. In this case, the patient couch 2 is also able to be adjusted via a corresponding drive mechanism or system 16.

The operation of the operating device 1 is controlled in this figure by a control device 18 shown in a console 17. The control device 18 is embodied for carrying out the method and in this example accordingly also realizes a collision protection system. The control device 18 further undertakes the control of the workflow. The console 17 is also supported so that it may move in this figure and has a sterile covered operating panel 19 and a display device 20. The operating panel 19 may also allow movements of various components, for example, the C-arm 5 as an image recording component, the robot arm 10, and/or patient couch 2 to be controlled. The operating panel 19 also has a confirmation operating element 21, the function of which will be explained in greater detail below.

The realization of the adaptive collision protection as a function of the operating phase in accordance with the operation workflow is to be explained in greater detail below in respect to FIG. 2 in an exemplary embodiment of the method. Both the workflow control, thus the monitoring and support of the operation workflow, and also the realization of the collision protection system are undertaken by the control device 18.

In act S1, the operation workflow begins for an operation of a patient 3. During the execution of the operation workflow, controlled and monitored as mentioned by the control device 18, said device constantly establishes, in act S2, current criticality information while evaluating the workflow data available. The criticality information in the present example is a criticality value that describes the criticality of possible collisions of components of the operating device 1 and/or movements of the patient 3 in relation to the interaction of the assistance robot 9 with the patient 3. The criticality increases, in particular, the more probable it is that a medical instrument 12 is being guided in the assistance component 11 and is penetrating into the patient 3, so that in this way a movement coupling between the patient 3 and the assistance component 11, thus with the assistance robot 9, is produced. In this case, the workflow data may already be present at least partly in the control device 18 as a result of the assisted workflow execution. Other workflow data may be established from sensor data from monitoring sensors and/or from image data of the image recording device 4 registered with the assistance robot 9, for example, by evaluating image data as to whether an instrument 12 has already penetrated into the patient 3. Monitoring sensors may have a contact switch in the assistance component 11 not shown in any greater detail here, which is actuated when an instrument 13 is guided in the assistance component 11, thus is coupled in terms of movement with the latter.

In an example workflow, the patient 3 may first be positioned on the patient couch 2, for example, wherein the other components of the operating device 1 are still at a distance from the patient 3 and are not being used, so that the safety requirements are quite low and the collision protection system may be operated in its normal operating mode, which also applies to any period of time that might be provided, in which a registration between the assistance robot 9 and the image recording unit 4 is established in relation to the patient 3. An increase in the criticality and thus in the criticality value occurs when the registration is concluded, because then the actual operation on the patient 3 may be started. Further increases in the criticality value are produced when a trajectory of the assistance component 11 approaching the patient 3, after the termination of which the instrument 12 is inserted, is ended and when the movement coupling of an instrument 12 with the assistance component 12 is established. Also, when it is detected from image data that the instrument 12 has penetrated into the patient 3, the criticality increases accordingly.

As explained, the criticality information established in act S2 ultimately describes how dangerous collisions are for the patient 3 as a result of the imminent or already existing movement coupling with the assistance robot 9. Accordingly, in act S3, it is checked as a criticality criterion whether the criticality value lies in a criticality interval assigned to the normal operating mode, (e.g., below a specific threshold value), or whether it is contained in at least one criticality interval that is assigned to a safe operating mode, in the event of a single safe operating mode if the previously stated threshold value is exceeded. If the criticality value is already located in the criticality interval that is assigned to the current operating mode of the collision protection system, then in accordance with the arrow 22, the execution sequence returns to act S2 and the criticality information is constantly further updated. If, however, a change of operating mode of the collision protection system is required, then in act S4 the operating mode is set, to which the criticality is assigned in which the current criticality of the criticality information lies. If the collision protection system is still in the normal operating mode and if the specific threshold value has been exceeded, a switch is made into the safe operating mode or into a safe operating mode and vice versa.

In this case, the safe operating mode is described below for the case in which only a single safe operating mode is used, in order to preserve the clarity of the description. In other exemplary embodiments, a number of operating modes are of course conceivable, in order to guarantee the suitable safety in a graduated and adapted manner, for example, a slight increase in the safety after conclusion of the registration between the image recording device 4 and the assistance robot 9, a further increase in the safety in a second safe operating mode on reaching the end point of the travel trajectory of the assistance robot 9 to the patient 3 as well as fulfilling the highest possible safety requirement (e.g., third safe operating mode), as soon as the instrument 13 is coupled in terms of movement with the assistance component 11 or is introduced into the patient 3.

Adaptations are undertaken from the normal operating mode to the safety mode (one in the example now being discussed), which greatly increase the safety of the collision protection, but may have the effect of slowing down the progress of the operation or the workflow, which is why, as a result of the interrogation in act S3, they are restricted to the cases in which they are actually needed.

Initially there is just provision in the safe operation mode for calculation processes for establishing collision values, which are to be evaluated later by measure criteria, on the one hand to be calculated redundantly, on the other more precisely. The redundant calculation is undertaken in a diversified manner here, by different processors, or at least processor cores being used for the redundant calculation paths, but also different software algorithms being used to establish the collision value. The results may be plausibility-checked against one another but also the collision protection system may continue to be operated if the calculation path fails. For more precise calculation, on the one hand, the calculation is reduced in this example to the components critical for the patient, which are grouped into a safety group, here the assistance component 11 (and thus the components coupled to it in terms of movement), the patient couch 2 and the C-arm 5 with the x-ray detector 7 and the x-ray emitter 6. The more precise calculation is manifested by spherical safety zones around the components or the patient not being used, but the surfaces of the components and of the patient 3 being described as surface meshes and also precise calculations taking place within the algorithms.

The safe operating mode further makes provision for the movement of components, (e.g., of the components of the safety group mentioned), only to be possible when a confirmation action of the operator is available. The confirmation action in this example is guaranteed via the confirmation operating element 21. This is constantly held during a manually controlled movement of a component, for example, of the patient couch 2, in order to ensure that the operator is aware of the critical situation and he is monitoring the operating process precisely. Should automatic operations be undertaken in the critical operation phase, the movement may initially be visualized by the display device 20, after which the user may carry out the confirmation operation action via the confirmation operation element 21.

In the safe operating mode, the speed of movement of the components, (e.g., of all components or of at least the components of the safety group), is greatly limited by an upper safety limit value. The safety limit value in this case is of course smaller than a normal limit value used in normal operating mode outside the safe operating mode. In the present example, the safety limit value in the safe operating mode is one millimeter per second, for example, so that an extremely slow movement that may be easily monitored is present, which moreover, in case of emergency, may be interrupted quickly and with short stop paths.

In safe operating mode, in the present example additional collision protection sensors 23 indicated in FIG. 1 are activated, in this example ultrasound distance measurement sensors, which are provided on the x-ray detector 7 (and if necessary also on the x-ray emitter 6) as image recording components or as part of an image recording component. The collision protection sensors 23 are not active in normal operating mode of the collision protection system, because they are directed to the operation region and, for example, may result in false triggers during hand movements of a person carrying out the operation. If the situation is more critical however, more account may be taken of such false triggers, in order to obtain a more reliable database for the calculation processes.

The collision values established in the calculation processes are evaluated by measure criteria for collision protection, wherein, when the corresponding measure criterion is fulfilled, a collision-avoiding measure and/or a warning measure is taken. In safe operating mode, the measure criteria and/or the measures may optionally be configured by adapting corresponding measure parameters, so that safety distances may be chosen larger, braking may be undertaken more quickly, earlier interventions may occur, and/or even additional measures and/or measure criteria may be employed in order to increase safety.

As has become evident, the safe operating mode satisfies far higher safety requirements, because the safety is greatly enhanced by a corresponding method of operation. This may, as mentioned, accordingly also occur in stages with a number of safe operating modes.

Although the disclosure has been illustrated and described in greater detail by the exemplary embodiments, the disclosure is not restricted by the disclosed examples and other variations may be derived herefrom by the person skilled in the art, without departing from the scope of protection of the disclosure. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A method for operating a collision protection system for a medical operating device, which has a patient couch for a patient to be operated on, an image recording device with at least one movable image recording component for recording image data of the patient during the operation, and an assistance robot having a movable assistance component situated at least temporarily inside the patient and/or is coupled in terms of movement to an instrument situated inside the patient during the operation, the method comprising:
determining an item of criticality information that describes a criticality of possible collisions of components of the medical operating device, movements of the patient in relation to an interaction of the assistance robot with the patient, or a combination thereof, wherein the determining takes into consideration a current operation phase, in workflow data describing an operation workflow; and
activating a safe operating mode of the collision protection system when the determined item of criticality information indicates a heightened criticality,
wherein the safe operating mode of the collision protection system satisfies a higher safety requirement than a normal operating mode.

2. The method of claim 1, further comprising:
switching back to a previous operating mode on fulfillment of a switching back criterion, use of a number of criticality criteria, or a combination thereof,
wherein, on fulfillment of a criticality criterion, a safe operating mode assigned to the switching back criterion is used.

3. The method of claim 2, wherein the heightened criticality is indicated when a predefined threshold value is exceeded, and
wherein the switching back criterion is when the criticality falls below the predefined threshold value.

4. The method of claim 1, wherein, in at least one safe operating mode of the at least one safe operating modes, at least one calculation process carried out within a framework of the collision protection system redundantly in relation to hardware and/or software,
wherein results obtained during the redundant at least one calculation process are taken into consideration for the collision protection system and/or are carried out with a greater calculation precision.

5. The method of claim 4, wherein the at least one calculation process is carried out to establish a probability of a collision.

6. The method of claim 1, wherein, in at least one safe operating mode of the at least one safe operating modes, a movement of at least one component of the medical operating device is only carried out after a confirmation action of an operator has been detected.

7. The method of claim 6, wherein the components of the medical operating device needing the confirmation action to be moved belong to a safety group of components.

8. The method of claim 7, wherein the safety group of components comprise the image recording device, the patient couch, and the movable assistance component.

9. The method of claim 1, wherein, in at least one safe operating mode of the at least one safe operating modes, a speed of movement of at least one component is limited by an upper safety limit value, which is less than a normal limit value used outside the safe operating mode.

10. The method of claim 1, wherein, in at least one safe operating mode of the at least one safe operating modes, at least one a measure parameter, describing an initiation of measures, of a measure criterion used in the collision protection system is configured to an earlier initiation by comparison with the normal operating mode.

11. The method of claim 1, wherein, in at least one safe operating mode of the at least one safe operating modes, at least one collision protection sensor deactivated in the normal operating mode is activated and sensor data of the at least one collision protection sensor is taken into account in calculation processes for the collision protection system.

12. The method of claim 1, wherein a central control device of the medical operating device monitoring progress of the operation is used, which establishes the workflow data.

13. The method of claim 12, wherein the workflow data is established at least in part from sensor data of a monitoring sensor monitoring an operation region, from image data of the image recording device registered with the assistance robot, or a combination thereof.

14. The method of claim 12, wherein the criticality information establishes an increased criticality for the workflow data describing a completed registration between the image recording device and the assistance robot, a conclusion of a trajectory of the movable assistance component moving towards the patient, a coupling in terms of movement of the instrument with the movable assistance component, or a combination thereof.

15. The method of claim 1, wherein, for reducing a calculation effort, the components of the medical operating device considered within a framework of calculation processes of the collision protection system are limited to a safety group of components,
wherein the safety group of components comprise the image recording device, the patient couch, and the movable assistance component.

16. The method of claim 1, wherein the heightened criticality is indicated when a predefined threshold value is exceeded.

17. A medical operating device comprising:
- a patient couch configured for a patient to be operated on;
- an image recording device having at least one movable image recording component configured to record image data of the patient during the operation;
- an assistance robot having a movable assistance component positioned at least temporarily inside the patient and/or is coupled in terms of movement to an instrument positioned inside the patient during the operation; and
- a control device configured to:
  - determine an item of criticality information that describes a criticality of possible collisions of components of the medical operating device, movements of the patient in relation to an interaction of the assistance robot with the patient, or a combination thereof, wherein the determining takes into consideration a current operation phase, in workflow data describing an operation workflow; and
  - activate a safe operating mode of a collision protection system when the determined item of criticality information indicates a heightened criticality,
  - wherein the safe operating mode of the collision protection system satisfies a higher safety requirement than a normal operating mode.

18. A medical operating device comprising:
- a control device having computer program, which when executed on control device, causes the medical operating device to:
  - determine an item of criticality information that describes a criticality of possible collisions of components of the medical operating device, movements of a patient in relation to an interaction of an assistance robot with the patient, or a combination thereof, wherein the determining takes into consideration a current operation phase, in workflow data describing an operation workflow, and
  - activate a safe operating mode of a collision protection system when the determined item of criticality information indicates a heightened criticality,
  - wherein the safe operating mode of the collision protection system satisfies a higher safety requirement than a normal operating mode.

* * * * *